United States Patent [19]

Scozzafava et al.

[11] Patent Number: 4,514,481

[45] Date of Patent: Apr. 30, 1985

[54] 4H-THIOPYRAN-1,1-DIOXIDE AND ELECTROPHOTOGRAPHIC LAYERS AND ELEMENTS COMPRISING SAME

[75] Inventors: Michael Scozzafava, Rochester; Chin H. Chen, Webster, both of N.Y.; George A. Reynolds, Gainesville, Ga.; Jerome H. Perlstein, Rochester, N.Y.

[73] Assignee: Eastman Kodak Company, Rochester, N.Y.

[21] Appl. No.: 588,169

[22] Filed: Mar. 9, 1984

[51] Int. Cl.$^3$ .......................... G03G 5/06; G03G 5/14
[52] U.S. Cl. ........................................ 430/58; 430/75; 549/13; 549/23
[58] Field of Search ............... 430/58, 75, 900; 549/12, 23

[56] References Cited

U.S. PATENT DOCUMENTS 3,905,814  9/1975  Crommentuyn et al. ...... 430/900 X
4,105,446  8/1978  Pu .......................................... 430/75

Primary Examiner—Roland E. Martin
Attorney, Agent, or Firm—John R. Everett

[57] ABSTRACT

Novel 4H-thiopyran-1,1-dioxides are disclosed. They are useful as electron transporters in electrophotographic layers and elements.

14 Claims, No Drawings

4H-THIOPYRAN-1,1-DIOXIDE AND ELECTROPHOTOGRAPHIC LAYERS AND ELEMENTS COMPRISING SAME

BACKGROUND OF THE INVENTION

Field of the Invention

The invention relates to new electron transporting compounds and electrophotographic compositions and elements comprising electron transporting compounds.

Electrophotographic layers and elements have been extensively described in both the patent and other literature. Generally, imaging processes involving these elements have in common the steps of electrostatically charging an electrophotographic element and exposing the element imagewise to electromagnetic radiation, thereby forming an electrostatic charge image. A variety of subsequent operations, well known in the art, can then be employed to produce a permanent record of the image.

Upon exposure of an electrostatically charged electrophotographic element, electron-hole pairs are formed in the electrophotographic layer of the element. When the element is electrostatically charged with a negative potential, the hole migrates to the surface of the electrophotographic layer thereby discharging the layer in the exposed areas. When the electrophotographic element is charged with a positive potential the electron migrates toward the surface of the electrophotographic layer thereby discharging the layer imagewise in the exposed areas.

Numerous electron donating organic photoconductive compounds are known which are effective in transporting holes to the surface of an electrophotographic layer. However, only a few electron accepting materials are effective in electron transport. An example is 2,4,7-trinitro-9-fluorenone (TNF). Thus, in most electrophotographic processes the electrophotographic element is initially charged to a negative potential.

There are applications in which it is more desirable to charge the electrophotographic element with a positive potential because of the lack of high quality negatively charged toners, such as in laser printing.

However, TNF is not equally effective as an electron transporting agent in all electrophotographic layers and elements designed for these uses. In addition, TNF is a known carcinogenic material.

SUMMARY OF THE INVENTION

The present invention provides an electrophotographic layer comprising an electrically insulating binder, and an electron donor characterized in that the composition also comprises, as an electron transporting compound, a 4H-thiopyran-1,1-dioxide having
  (a) an electron withdrawing group in the 4-position; and
  (b) a half wave reduction potential more positive than $-0.5$ volts as measured against a saturated calomel electrode.

The 4H-thiopyran-1,1-dioxides are effective electron-transport compounds in electrophotographic layers and elements. 4H-thiopyran-1,1-dioxides having a half wave reduction potential less positive then $-0.5$ volts do not measurably transport electrons. In some embodiments of this invention the 4H-thiopyran-1,1-dioxides are comparable or show unexpected advantages over TNF as electron-transporters.

In a preferred embodiment the present invention provides an electrophotographic element having at least two layers comprising a charge-generating electrophotographic layer in electrical contact with a charge-transport layer characterized in that the charge-transport layer compises a 4H-thiopyran-1,1-dioxide having
  (a) an electron withdrawing group in the 4-position
  (b) a half wave reduction potential more positive than $-0.5$ volts as measured against a saturated calomel electrode.

Preferred 4H-thiopyran-1,1-dioxides have the structure

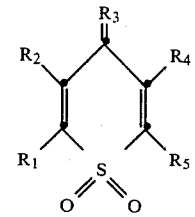

wherein
$R_3$ represents an electron withdrawing group;
$R_1$ and $R_5$ each independently represents alkyl or aryl;
$R_2$ and $R_4$ each independently represents hydrogen or an alkoxy carbonyl group; or
$R_1$ and $R_2$ or $R_4$ and $R_5$ together with the carbon atoms to which they are attached form a fused unsaturated 6-membered ring.

The thiopyran-1,1-dioxides wherein the electron withdrawing group is other than oxo are new compounds.

In the above structural formula alkyl refers to straight- or branched-chained alkyl groups having from 1 to 16 carbon atoms such as methyl, isopropyl, t-butyl, octyl, neopentyl, tridecyl and hexadecyl. Aryl refers to substituted and unsubstituted aryl groups such as phenyl, naphthyl, anthracenyl, methyl phenyl and t-butyl phenyl.

Useful electron withdrawing groups include Meldrum's acid, oxo, dicyanomethylene, indandionemethylene, ethoxycarbonyl cyanomethylene, bis(phenylsulfonyl)methylene, cyanophenylsulfonyl methylene, cyanodiphenylphosphinyl and bis(ethoxycarbonyl)methylene.

DETAILS OF THE INVENTION

In general, 4H-thiopyran-1,1-dioxides are prepared by reacting tetrahydro-4H-thiopyrane-4-ones with peracetic acid in an inert solvent to form the corresponding sulfones which are collected and subsequently oxidized with dimethyl sulfoxide in the presence of a catalytic amount of iodine and $H_2SO_4$ to form the thiopyran-4-one-1,1-dioxides. The latter compounds can be converted to other derivatives using Knoevenagel condensation. The latter condensation involves the reaction of an active compound such as malononitrile, 1,3-indandione and Meldrum's acid with thiopyran-1,1-dioxides in the presence of a catalytic amount of base in protic solvent.

The following preparative examples are presented to illustrate the preparation of the electron transporting thiopyran-1,1-dioxide. The structure and composition of the compounds, presented in Table I infra, were confirmed by H-NMR spectra, CMR spectra, Mass spectra, field desorption Mass spectra, microanalysis, melting points, UV spectra and IR spectra. Half wave reduction potentials were measured against a saturated calomel electrode (SCE).

EXAMPLE 1

Preparation of
2,6-diphenyl-4H-thiopyran-4-one-1,1-dioxide
Intermediate

A stirred solution of 26.8 gm (0.1 mol) of 2,6-diphenyl-2,3,5,6-tetrahydro-4H-thiopyran-4-one in 125 ml of methylene chloride was slowly added to 30 ml of 40% peracetic acid with external cooling to keep the temperature below 30° C. The solution was stirred overnight during which time it became a solid cake. 2,6-Diphenyl-tetrahydro-4H-thiopyran-4-one-1,1-dioxide was collected and washed thoroughly with methanol. This solid was dissolved in 100 ml of dimethylsulfoxide. One gram of iodine and 0.5 ml of sulfuric acid were added to the solution. The mixture was heated on a steam bath for 24 hours, cooled to room temperature and poured into 100 ml of water. The mixture was stirred for 2 hours and a solid was collected and washed with water and then methanol. The product was recrystallized from toluene giving 24.0 gm of the titled compound (mp 145°–146° C.).

EXAMPLE 2

Preparation of
4-dicyanomethylene-2,6-diphenyl-4H-thiopyran-1,1-dioxide (Compound 3, Table I)

A mixture of 8 gm (0.0464 mol) of 2,6-diphenyl-4H-thiopyran-4-one-1,1-dioxide of Example 1, 3.1 gm (0.047 mol) of malononitrile, 50 ml of alcohol and 20 drops of piperidine was refluxed for 1 hour. The reaction mixture was cooled to room temperature and the title compound was collected and recrystallized from 100 ml of toluene (mp 216°–217° C.).

EXAMPLE 3

Preparation of
2,6-diphenyl-4-(2,2-dimethyl-m-dioxane-4,6-dione-5-ylidene)-4H-thiopyran-1,1-dioxide (Compound 1, Table I)

A mixture of 1.32 gm (5 mmol) of the Compound of Example 1, 0.80 gm (5.5 mmol) of Meldrum's acid, 10 ml of alcohol and 5 drops of piperidine was refluxed for 1 hour, allowed to stand overnight and the yellow solid titled compound was collected. The solid was recrystallized from alcohol (mp 214°–215° C.).

EXAMPLE 4

Preparation of
2,6-diphenyl-4-(1,3-indandione-2-ylidene)-4H-thiopyran-1,1-dioxide (Compound 2, Table I)

A mixture of 1.0 gm (3.38 mmol) of Compound 1, Table I, 0.50 gm (3.4 mmol) of 1,3-indandione, 4 drops of piperidine and 50 ml of methanol was heated on a steam bath for 30 minutes, cooled to room temperature and the titled compound collected (mp 235°–236° C.).

EXAMPLE 5

Preparation of
2,6-Di-tert-butyl-4-dicyanomethylene-4H-thiopyran-1,1-dioxide (Compound 5, Table I)

A mixture of 3.0 gm (13.4 mmol) of 2,6-ditert-butyl-4H-thiopyran-4-one and 5 ml of peracetic acid (40%) was heated on a steam bath for 15 minutes, cooled, diluted with a small amount of alcohol and chilled. The solid was collected and recrystallized from alcohol giving 1.93 gm of 2,6-di-tertbutyl-4H-thiopyran-4-one-1,1-dioxide (mp 105°–106° C.).

A mixture of 1.53 gm (6 mmol) of the recrystallized solid, 0.66 gm (10 mmol) of malononitrile, 5 ml of alcohol and 3 drops of piperidine was refluxed for 1 hour, chilled and the white needles were collected. The title compound was recrystallized from alcohol (mp 202°–203° C.).

EXAMPLE 6

Preparation of 3,5-bis
carbomethoxy)2,6-diphenyl-4H-thiopyran-4-one-1,1-dioxide (Compound 6, Table I)

A mixture of 2 gm (5.2 mmol) of 2,6-diphenyl-3,5-dicarbomethoxy-4H-thiopyran-4-one in 10 ml of 40% peracetic acid was heated on a steam bath for 1 hour. On cooling to room temperature, yellowish long needles of the titled compound crystallized from the yellow solution, filtered and washed with acetic acid (mp 202°–4° C.).

Compounds 6 and 7 of Table I (Examples 7 and 8 infra) were made by methods which differ from the general procedure described hereinbefore.

EXAMPLE 7

Preparation of
2,6-Diphenyl-4-(cyanoethoxycarbonylmethylene)-4H-thiopyran-1,1-dioxide (Compound 6, Table I)

A solution of 6.6 ml (0.06 M) of $TiCl_4$ in 15 ml of $CCl_4$ was added dropwise to 120 ml of ice-cooled dry THF (120 ml) under argon. The resulting bright yellow suspension was added quickly to a solution of 8.9 gm (0.03 M) of 2,6-diphenyl-4H-thiopyran-4-one-1,1-dioxide and 3.4 gm (0.03 M) of ethyl cyanoacetate in 70 ml of THF. The mixture was stirred for 20 minutes in the ice-bath. Then 9.5 gm (0.12 M) of dry pyridine was then added. After stirring at room temperature overnight 30 ml of $H_2O$ and a small amount of ether was added to the reaction mixture. The organic phase was separated, washed with dilute $NaHCO_3$, brine, dried ($MgSO_4$) and rotavaporated to give 11.4 gm of a highly fluorescent yellow solid. The latter solid was recrystallized from toluene containing a little hexane to give the titled compound (mp 156°–7° C.).

EXAMPLE 8

Preparation of
4-dicyanomethylene-2,6-dimethyl-4H-thiopyran-1,1-dioxide (Compound 7, Table I)

A mixture of 2.8 gm of 2,6-dimethyl-4H-thiopyran-4-one, 1.5 gm of malononitrile and 20 ml of acetic anhydride was refluxed for 1 hour, chilled and collected as the solid intermediate, 4-dicyanomethylene-2,6-dimethyl-4H-thiopyran.

Two grams of this intermediate and 15 ml of 40% peracetic acid (added portionwise) were heated on a steam bath. A pale yellow crystalline solid slowly separated and the mixture was let stand overnight in a beaker to allow the solvent to evaporate. The residue was slurried with ethanol, chilled and the solid was collected and recrystallized from methanol to give. the title compound (mp 176°–177° C.).

The 4H-thiopyran-1,1-dioxides prepared according to the foregoing procedures are presented in Table I.

TABLE I

| Compound | Acceptor | $E^o_{\frac{1}{2}}{}^a$ (volts) |
|---|---|---|
| 1 | 2,6-diphenyl-4-(2,2-dimethyl-m-dioxane-4,6-dione-5-ylidene)-4H—thiopyran-1,1-dioxide | −0.10 |
| 2 | 2,6-diphenyl-4-(1,3-indandione-2-ylidene)-4H—thiopyran-1,1-dioxide | −0.17 |
| 3 | 4-dicyanomethylene-2,6-diphenyl-4H—thiopyran-1,1-dioxide | −0.13 |
| 4 | 2,6-di-tert-butyl-4-dicyanomethylene-4H—thiopyran-1,1-dioxide | −0.40 |
| 5 | 3,5-bis(carbomethoxy)-2,6-diphenyl-4H—thiopyran-4-one-1,1-dioxide | −0.43 |
| 6 | 2,6-diphenyl-4-(cyanoethoxycarbonylmethylene)-4H—thiopyran-1,1-dioxide | −0.36 |
| 7 | 2,6-dimethyl-4-dicyanomethylene-4H—thiopyran-4-one-1,1-dioxide | −0.41 |

$^a$Half wave reduction potential at Pt electrode vs saturated calomel electrode in $CH_3CN$.

The electron transporting 4H-thiopyran-1,1-dioxides are useful in both single layer and multilayer electrophotographic elements.

In single layer electrophotographic elements the electron transporting compound is combined with small amounts of an electron donor to initiate the charge-generation step. In such single layer elements, the 4H-thiopyran-1,1-dioxide serves both as one component of the charge-generating coupler as well as the charge-transporting compound.

The single layer electrophotographic elements can be prepared by blending a dispersion or solution of a small amount of an electron donor together with an 4H-thiopyran-1,1-dioxide, and an electrically insulating film-forming binder. The resulting composition is then coated on a support to form the element.

The amount of 4H-thiopyran-1,1-dioxide necessary to provide effective electron transport activity can vary widely. The optimum concentration in any given case will vary with the specific donor and specific 4H-thiopyran-1,1-dioxide. Preferably, the coated layer comprises from 10 to 50 weight percent of the thiopyran-1,1-dioxide and 0.01 to 50 weight percent of the electron donor.

The 4H-thiopyran-1,1-dioxide compounds are effective as electron transporters with a wide variety of electron donors. Useful electron donors include:

1. arylamine photoconductors including substituted and unsubstituted arylamines, diarylamines, nonpolymeric triarylamines and polymeric triarylamines such as those described in U.S. Pat. Nos. 3,240,597 by Fox, issued Mar. 15, 1966 and 3,180,730 by Klupfel et al, issued Apr. 27, 1965;
2. polyarylalkane photoconductors of the types described in U.S. Pat. Nos. 3,274,000 by Noe et al, issued Sept. 20, 1966; 3,542,547 by Wilson, issued Nov. 24, 1970 and 3,542,544 by Seus et al, issued Nov. 24, 1970;
3. 3-diarylamino-substituted chalcones of the types described by Fox, U.S. Pat. No. 3,526,501 issued Sept. 1, 1970;
4. nonionic cycloheptenyl compounds of the types described by Looker, U.S. Pat. No. 3,533,786 issued Oct. 13, 1970;
5. compounds containing an:

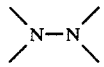

nucleus, as described by Fox, U.S. Pat. No. 3,542,546 issued Nov. 24, 1970;

6. organic compounds having a 3,3'-bisaryl-2-pyrazoline nucleus, as described by Fox et al, U.S. Pat. No. 3,527,602 issued Sept. 8, 1970;

7. triarylamines in which at least one of the aryl radicals is substituted by either a vinyl radical or a vinylene radical having at least one active hydrogen-containing group, as described by Brantly et al, U.S. Pat. No. 3,567,450 issued Mar. 2, 1971;

8. triarylamines in which at least one of the aryl radicals is substituted by an active hydrogen-containing group, as described by Brantly et al, Belgian Pat. No. 728,563 dated Apr. 30, 1971;

9. any other organic electron donor compound which exhibits photoconductive properties such as those set forth in Australian Pat. No. 248,402 and the various polymeric photoconductors such as the photoconductive carbazole polymers described in U.S. Pat. No. 3,421,891, issued Jan. 14, 1969.

The thiopyran-1,1-dioxides of the invention are also useful in so-called multi-layer electrophotographic elements. Such elements have at least two layers comprising a charge-transport layer in electrical contact with a charge-generation layer. Both the charge-generation layer and the charge-transport layer may include an electrically insulating binder.

Such multi-layer elements are well known in the electrophotographic art and thus need not be discussed in detail here. Berwick et al's U.S. Pat. No. 4,175,960 issued Nov. 27, 1979 describes in detail an especially useful arrangement for multi-layer elements. The disclosure of Berwick et al is expressly incorporated herein by reference.

The charge-transport layer comprises one or more 4H-thiopyran-1,1-dioxides in a suitable electrical insulating film-forming polymeric binder. The binder material is an electrically insulating material which help to provide the charge-transport layer with electrical insulating characteristics, and it also serves as a film-forming material useful in (a) coating the charge-transport layer, (b) adhering the charge-transport layer to an adjacent substrate, and (c) providing a smooth, easy to clean, and wear resistant surface.

As the electron transporter, the 4H-thiopyran-1,1-dioxide included in the charge-transport layer is insensitive or, at most, only partially sensitive to the exposing radiation. Thus, the 4H-thiopyran-1,1-dioxide is selected so that it absorbs substantially no exposing radiation.

In general, it has been found that, when a binder is employed, useful results are obtained wherein the amount of active 4H-thiopyran-1,1-dioxide electron-transporter contained within the charge-transport layer varies within the range of from about 10 to about 50 percent based on the dry weight of the charge-transport layer.

The charge-transport layer may also contain other addenda such as leveling agents, surfactants, plasticizers, and the like to enhance or improve various physical properties of the charge-transport layer. In addition, various addenda to modify the electrophotographic response of the element may be incorporated in the charge-transport layer. For example, various contrast control materials, such as certain electron-trapping agents and certain easily oxidized dyes may be incorporated in the charge-transport layer. Various such contrast control materials are described in *Research Disclosure*, Vol. 122, June 1974, page 33, in an article entitled "Additives for Contrast Control in Organic Photoconductor Compositions and Elements", published by Kenneth Mason Publications Limited, Emsworth, Hampshire PO10 7DD, United Kingdom.

The thickness of the charge-transport layer may vary. It is especially advantageous to use a charge-transport layer which is thicker than that of the charge-generation layer, with best results generally being obtained when the charge-transport layer is from about 5 to about 200 times and particularly 10 to 40 times as thick as the charge-generation layer. A useful thickness for the charge-generation layer is within the range of from about 0.1 to about 15 microns dry thicknesss, particularly from about 0.5 to about 2 microns. However, good results can also be obtained using a charge-transport layer which is thinner than the charge-generation layer.

The charge-transport layers described herein are generally applied to the desired substrate by coating a liquid dispersion or solution containing the charge-transport layer components. Generally, the liquid coating vehicle used is an organic vehicle. Organic coating vehicles include (1) aromatic hydrocarbons such as benzene, naphthalene, etc., including substituted aromatic hydrocarbons such as toluene, xylene, mesitylene, etc.;

(2) ketones such as acetone, 2-butanone, etc.;

(3) halogenated aliphatic hydrocarbons such as methylene chloride, chloroform, ethylene chloride, etc.;

(4) ethers including cyclic ethers such as tetrahydrofuran, ethylether; and (5) mixtures of the above.

The charge-generation layer can be formed with a wide variety of known charge-generating electrophotographic materials. Any spectral sensitizer could serve as the active component of the charge-generating layer. Particular suitable materials include selenium, chloroindiumphthalocyanine chloride, and heterogeneous (aggregate) electrophotographic compositions described in Light, U.S. Pat. No. 3,615,414, issued Oct. 26, 1971. Methods of making and coating such charge-generation layers are well known in the electrophotographic arts and need not be described in detail here.

A partial listing of representative materials which may be employed as the electrically insulating film-forming binders in the various layers of the electrophotographic elements described herein include styrenyl-butadiene copolymers; polyvinyl toluene-styrene copolymers; styrene-alkyd resins; silicone-alkyd resins; soya-alkyd resins; vinylidene chloride-vinyl chloride copolymers; poly(vinylidene chloride); vinylidene chloride-acrylonitrile copolymers; vinyl acetate-vinyl chloride copolymers; poly(vinyl acetals), such as poly(vinyl butyral); nitrated polystyrene; polymethylstyrene; isobutylene polymers; polyesters, such as poly[ethylene-co-alkylenebis(alkyleneoxyaryl)phenylenedicarboxylate]; phenolformaldehyde resins; ketone resins; polyamides; polycarbonates; polythiocarbonates; poly[ethylene-co-isopropylidene-2,2-bis(ethyleneoxyphenylene)-terephthalate]; copolymers of vinyl haloarylates and vinyl acetate such as poly(vinyl-m-bromobenzoate-covinyl acetate); chlorinated poly(olefins), such as chlorinated poly(ethylene); etc. Methods of making resins of this type have been described in the prior art. For example, styrenealkyd resins can be prepared according to the method described in Gerhart U.S. Pat. No. 2,361,019, issued Oct. 24, 1944 and Rust U.S. Pat. No. 2,258,423, issued Oct. 7, 1941. Suitable resins of the type contemplated for use in the charge-transport layers of the invention are sold under such tradenames as VITEL PE-101, CYMAC, Piccopale 100, Saran F-220, and LEXAN 145.

The elements are useful in electrophotographic processes. Such processes generally employ a single layer or a multilayer electrophotographic element. The element is first given a uniform surface charge after a suitable period of dark adaptation. The element is then exposed to a pattern of actinic radiation which has the effect of differentially reducing the potential of the surface charge in accordance with the relative energy contained in various parts of the radiation pattern. The differential surface charge or electrostatic latent image remaining on the element is then made visible by contacting the surface with a suitable electroscopic marking material (toner).

The marking material, whether contained in an insulating liquid or on a dry carrier, is deposited on the exposed surface in accordance with either the charge pattern or the absence of charge pattern as desired. The deposited marking material is then either permanently fixed to the surface of the sensitive element by known means such as heat, pressure and solvent vapor, or transferred to a second support to which it is similarly fixed.

The electrostatic latent image can be transferred to a second support and developed there.

The following examples (9-15) are presented to demonstrate the capability of the dioxide compounds used in the invention in transporting electrons and thereby effectively discharging an electrophotographic element.

EXAMPLES 9-10

Two different electrophotographic elements were prepared by first dissolving sufficient quantities of the electron-transporting 4H-thiopyran-1,1-dioxide and tri-p-tolylamine in dichloromethane (DCM) to provide a dried electrophotographic layer containing 30% by weight of the selected dioxide and 1.0% by weight of the tri-p-tolylamine. A sufficient amount of a stock solution containing Lexan 145 TM polycarbonate (General Electric) in DCM was added to the solution to obtain a dried layer comprising about 60% by weight of Lexan 145 TM. The solution was stirred for several minutes and then coated at 150 μm wet thickness on a conductive poly(ethylene terephthalate) support containing a CuI conductive layer. A barrier layer of cellulose nitrate was coated between the conductive support and the electrophotographic layer.

Each element was corona-charged to a negative surface potential equivalent to the field strengths, $E_o$, indicated in Table II. Each element was then exposed to monochromatic radiation at the wavelength indicated in Table II. The incident photon flux (I) was measured with an Optronics Laboratories Model 730-A Radiometer. Films were allowed to discharge while exposed to the radiation. The photodischarge sensitivity, $S_i$, was determined by allowing the elements to discharge from $E_o$ to $E_o/2$. The amount of radiation necessary to produce this discharge was then calculated from the time required for this half-decay and the incident photon flux.

Table II shows photosensitivity ($S_i$) for the electrophotographic elements of the invention (Compounds 1 and 3).

The photosensitivity measurements show that both compounds 1 and 3 are effective as electron-transporters. This data demonstrates the electron-transporting capabilities of 4H-thiopyran-1,1-dioxide compounds used in this invention.

TABLE II

| Example | Table I 4H—Thiopyran-1,1-Dioxide (Table I) | $\lambda(nm)^a$ | Initial Field $E_o$ (V/cm) | $S_i{}^b$ (ergs/cm$^2$) |
|---|---|---|---|---|
| 9 | Compound 1 | 380 | $-1.0 \times 10^6$ | 1582 |
| 10 | Compound 3 | 380 | $-1.0 \times 10^6$ | 210 |

$^a$Measuring wavelength for which film O.D. <2.
$^b$Speed for half-decay at λ, negative charging front surface exposure.

EXAMPLES 11-14

Four different multi-layer electrophotographic elements were prepared.

Each element was prepared as follows:

Each of the completed elements comprised a dried 1.0 μm thick charge-generation layer containing, on a weight to weight basis, 52.5% Lexan 145, 27.5% 4-(4-(dimethylamino)phenyl)-2,6-diphenylthiopyrylium hexafluorophosphate and 20% tri-p-tolylamine coated on a nickel subbed poly(ethyleneterephthalate) support. The coated charge-generation layer was vapor treated with warm toluene causing the layer to aggregate as taught in U.S. Pat. No. 3,615,414 to form an electrophotographic charge-generating layer.

A charge-transport layer was coated over the charge-generation layer from chloroform. The solution was stirred for one-half hour and then coated at 150 μm wet thickness on the charge-generation layer. The dried charge-transport layer contained 30% by weight of a 4H-thiopyran-1,1-dioxide in Lexan 145. The entire multi-layer element was 7 to 11 μm thick.

Photosensitivity was determined as in Examples 9-10 supra except the front surface of the elements were positively charged prior to exposure.

Light passing through the charge-transport layer and absorbed by the charge-generation layer leads to generation of electron-hole pairs at the charge-generation layer, charge-transport layer interface. If the front surface of the film is charged positively, electrons, if they are effectively transported through the charge-transport layer, will discharge the positive front surface of the element. If the electrons are not effectively transported, little or no discharge of the film is observed.

Table III presents data for four 4H-thiopyran-1,1-dioxides used in four different charge transport layers in the multi-layer format. The elements containing Compounds 3 and 4 of Table I had discharge speeds for half decay comparable to films containing TNF as an electron transport material.

The results of these examples show that the electron-transporting 4H-thiopyran-1,1-dioxides effectively transport electrons in multi-layer photoconductive elements.

TABLE III

Multi-Active Electrophotographic Elements
Having Charge-Transport Layers
Containing a 4H—Thiopyran-1,1-Dioxide

| Example | Table I Compound No. | Initial Field $E_o$ (V/s) | $S_{\frac{1}{2}}$ (ergs/cm$^2$) | $\lambda$ |
|---|---|---|---|---|
| 11 | 3 | $5.4 \times 10^5$ | 68 | 670 nm |
| 12 | 4 | $5.4 \times 10^5$ | 42 | 670 nm |
| 13 | 5 | $9.0 \times 10^5$ | >1000 | 670 nm |
| 14 | 7 | $7.4 \times 10^5$ | 100 | 670 nm |

EXAMPLE 15

In this example the prepared electrophotographic element includes a charge-generation layer of 0.26 μm of evaporated selenium on a nickel-subbed poly(ethylene terephthate) support. The charge-transport layer containing Compound 4, Table I, was evaporated (1.24 μm thick) over the charge-generation layer. Photosensitivity data, as determined in Examples 9-14, is summarized in Table IV. Exposure was at 450 nm. This data shows that Compound 4, Table I is an extremely effective electron transporter in multi-layer electrophotographic elements.

TABLE IV

| Example No. | Acceptor | Initial Field $E_o$ (V/cm) | Dark Decay (V/sec) | $S_{\frac{1}{2}}$ ergs/cm$^2$ |
|---|---|---|---|---|
| 15 | 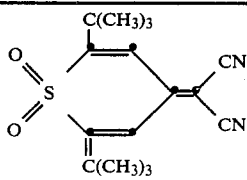 | $1.3 \times 10^6$ | 3 | 10 |

The invention has been described in detail with particular reference to preferred embodiments thereof, but it will be understood that variations and modifications can be effected within the spirit and scope of the invention.

We claim:

1. An electrophotographic layer comprising an electrically insulating binder, and an electron donor characterized in that the composition also comprises a 4H-thiopyran-1,1-dioxide having
   (a) an electron withdrawing group in the 4-position and
   (b) a half wave reduction potential more positive than −0.5 volts as measured against a saturated calomel electrode.

2. The layer of claim 1 wherein the 4H-thiopyran-1,1-dioxide has the structure

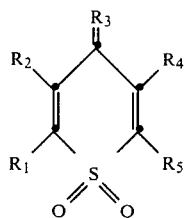

wherein $R_3$ represents an electron withdrawing group;

$R_1$ and $R_5$ each independently represents alkyl or aryl;

$R_2$ and $R_4$ each independently represents hydrogen or an alkoxy carbonyl group; or $R_1$ and $R_2$ or $R_4$ and $R_5$ together with the carbon atoms to which they are attached form a fused unsaturated 6-membered ring.

3. The layer of claim 2 wherein
$R_3$ represents oxo, dicyanomethylene, indandionemethylene or cyanoethoxycarbonylmethylene;

$R_1$ and $R_5$ each independently represents phenyl, methyl or t-butyl;

$R_2$ and $R_4$ each independently represents hydrogen or methoxycarbonyl; or $R_1$ and $R_2$ taken together with the carbon atoms to which they are attached form a fused 6-member unsaturated ring.

4. The layer of claim 2 wherein the 4H-thiopyran-1,1-dioxide is selected from the group consisting of 4-dicyanomethylene-2,6-diphenyl-4H-thiopyran-1,1-dioxide, 2,6-di-tert-butyl-4-dicyanomethylene-4H-thiopyran-1,1-dioxide and 2,6-dimethyl-4-dicyanomethylene-4H-thiopyram-4-one-1,1-dioxide.

5. The layer of claim 2 comprising from 0.01 to 50 weight percent of the electron donor and from 10 to 50 weight percent of the 4H-thiopyran-1,1-dioxide.

6. An electrophotographic element comprising a charge-generating electrophotographic layer in electrical contact with a charge-transport layer characterized in that the charge-transport layer comprises a 4H-thiopyran-1,1-dioxide having
   (a) an electron withdrawing group in the 4-position and
   (b) a half wave potential more positive than −0.5 volts as measured against a saturated calomel electrode.

7. The electrophotographic element of claim 6 wherein the 4H-thiopyran-1,1-dioxide has the structure

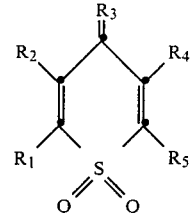

wherein $R_3$ represents an electron withdrawing group;

$R_1$ and $R_5$ each independently represents alkyl or aryl;

$R_2$ and $R_4$ each independently represents hydrogen or an alkoxy carbonyl group; or $R_1$ and $R_2$ or $R_4$ and $R_5$ together with the carbon atoms to which they are attached form a fused unsaturated 6-membered ring.

8. The electrophotograpnic element of claim 6 wherein the 4H-thiopyran-1,1-dioxide is selected from the group consisting of 4-dicyanomethylene-2,6-diphenyl-4H-thiopyran-1,1-dioxide, 2,6-di-tert-butyl-4-dicyanomethylene-4H-thiopyran-1,1-dioxide and 2,6-dimethyl-4-dicyanomethylene-4H-thiopyran-4-one-1,1-dioxide.

9. The electrophotographic element of claims 6 or 7 wherein the charge-generating layer is selected from the group consisting of a selenium layer, a chloroindiumphthalocyanine chloride layer and a heterogeneous conductive layer and the charge-transport layer comprises a 4H-thiopyran-1,1-dioxide selected from the group consisting of 4-dicyanomethylene-2,6-diphenyl-4H-thiopyran-1,1-dioxide, 2,6-di-tert-butyl-4-dicyanomethylene-4H-thiopyran-1,1-dioxide and 2,6-dimethyl-4-dicyanomethylene-4H-thiopyran-4-one-1,1-dioxide.

10. The electrophotographic elements of claims 6 or 7 wherein the charge-transport layer comprises from 10 to 50 weight percent 4H-thiopyran-1,1-dioxide.

11. A 4H-thiopyran-1,1-dioxide having an electron withdrawing group other than oxo in the 4-position and a half wave reduction potential more positive than −0.5 volts as measured against a calomel electrode.

12. The compound of claim 11 having the structure

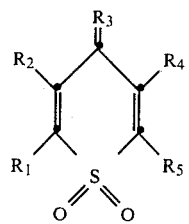

wherein
$R_3$ represents an electron withdrawing group other than oxo;
$R_1$ and $R_5$ each independently represents alkyl or aryl;
$R_2$ and $R_4$ each independently represents hydrogen or an alkoxy carbonyl group; or
$R_1$ and $R_2$ or $R_4$ and $R_5$ together with the carbon atoms to which they are attached form a fused unsaturated 6-membered ring.

13. The compound of claim 12 wherein
$R_3$ represents dicyanomethylene, indandionemethylene, cyanoethoxycarbonylmethylene;
$R_1$ and $R_5$ each independently represents phenyl, methyl and t-butyl;
$R_2$ and $R_4$ each independently represents hydrogen or methoxycarbonyl; or
$R_4$ and $R_5$ taken together with the carbon atoms to which they are attached form a fused 6-member unsaturated ring.

14. The compound of claim 12 selected from the group consisting of 4-dicyanomethylene-2,6-diphenyl-4H-thiopyran-1,1-dioxide, 2,6-di-tertbutyl-4-dicyanomethylene-4H-thiopyran-1,1-dioxide and 2,6-dimethyl-4-dicyanomethylene-4H-thiopyran-4-one-1,1-dioxide.

* * * * *